Jan. 19, 1960 H. C. SWIM Plant Pat. 1,897
ROSE PLANT
Filed April 20, 1959
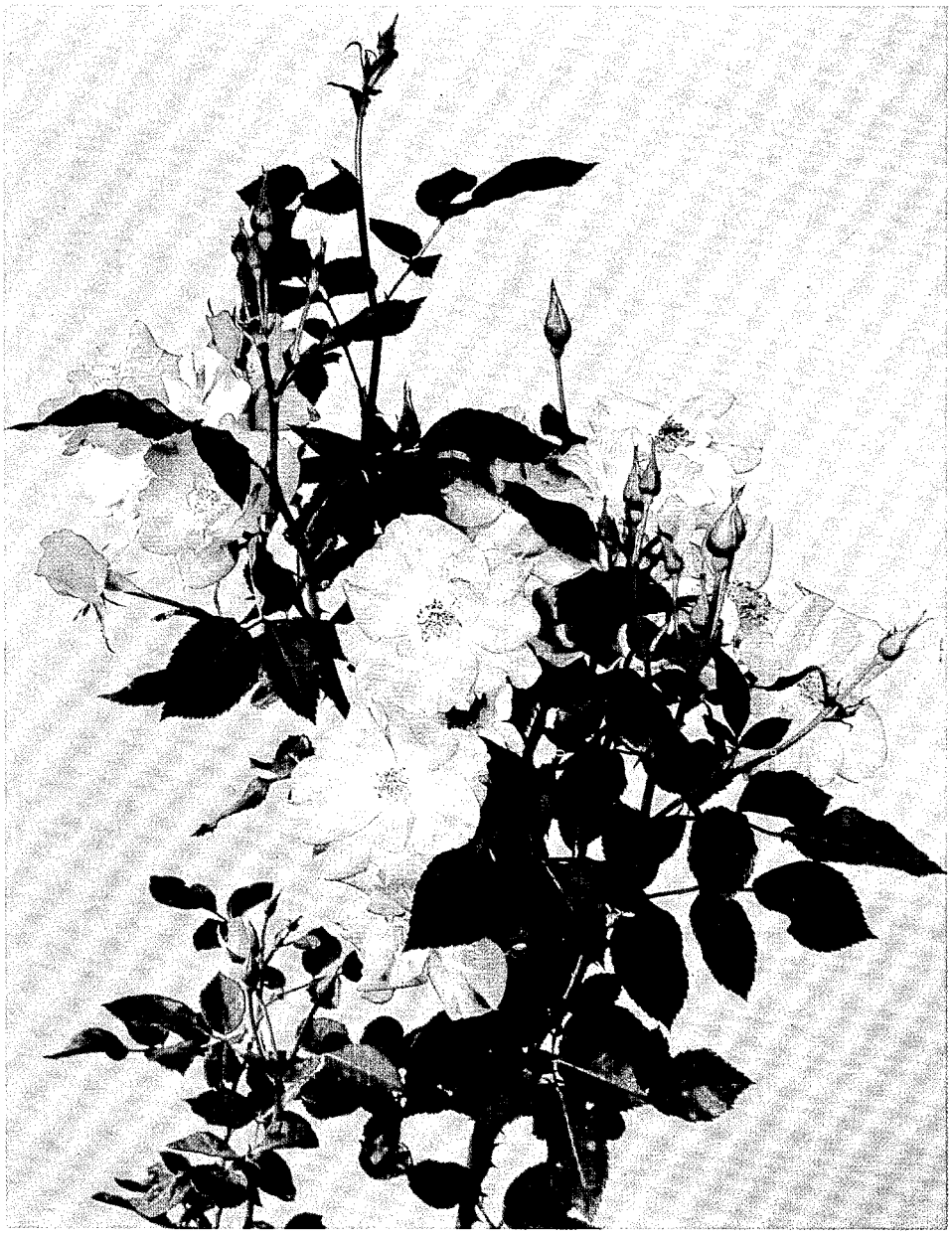
Inventor.
H. C. Swim
By: Robb & Robb
Attorneys.

United States Patent Office

Plant Pat. 1,897
Patented Jan. 19, 1960

1,897

ROSE PLANT

Herbert C. Swim, Ontario, Calif., assignor to Armstrong Nurseries, Inc., Ontario, Calif., a corporation of California Application April 20, 1959, Serial No. 807,741

1 Claim. (Cl. 47—61)

The present invention relates to a new and distinct variety of rose plant of the floribunda class, which was originated by me by crossing the variety "Frolic" (Plant Patent No. 1,179) with the variety "Pink Bountiful" (Plant Patent No. 601).

The general objective of this breeding was to produce an improved pink floribunda rose which combines the compact, well-shaped densely foliaged, and very floriferous plant habits of the parent variety "Frolic" with the greater vigor, larger foliage, and the larger and better-shaped flower characteristics of "Pink Bountiful." This objective was fully achieved, along with other desirable improvements, as evidenced by the following unique combination of characteristics which are outstanding in the new variety and which distinguish it from its parents, as well as from all other varieties of which I am aware:

(1) A vigorous, bushy, much-branched, well-shaped plant habit;

(2) Attractive, medium-sized, disease-resistant, dark green foliage;

(3) A floriferousness which is better than the average floribunda rose, and resulting in literally covering the plant with flowers at peak bloom; and (4) Attractive, medium-size, rather flat flowers varying from a medium to dark pink general color tonality when first open, and fading to a very light pink color as the petals drop, thus presenting a pleasing contrast of light and dark pink colors.

In comparison with its seed parent, "Frolic," the plant of my new variety is more vigorous in its habit of growth and has somewhat larger foliage than that of its parent; and the flowers of the new variety are somewhat larger and have fewer petals.

As compared with its pollen parent, "Pink Bountiful," the new variety is more floriferous, and its flowers are semi-double instead of very double, like those of this parent.

Asexual reproduction of my new variety by budding, as performed at Ontario, California, shows that the foregoing characteristics and distinctions come true to form and are established and transmitted through succeeding propagations.

The accompanying drawings show typical specimens of the vegetative growth and flowers of my variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway") as indicated:

Type: Bush; outdoor; seedling; for cut flowers and for garden decoration.

Class: Floribunda.

Breeding: Seedling.

*Seed parent.*—"Frolic."

*Pollen parent.*—"Pink Bountiful."

Propagation: Holds its distinguishing characteristics through succeeding propagations by budding.

*Flower*

Locality where grown and observed: Ontario, California.

Flowers borne: Usually from 3 to 5 or more to stem; in somewhat irregular clusters; on short stems of normal strength.

Quantity of bloom: Very abundant, outdoors.

Continuity: Nearly continuous during growing season.

Fragrance: From none to slight.

Bud:

*Peduncle.*—Average length; from slender to average caliper; erect; usually smooth; with few stipitate glands. Color—Near Apple Green, Plate XVII (Ridgway).

*Before calyx breaks.*—Size—small. Form—medium length; pointed; ovoid.

*As calyx breaks.*—Color—between Crimson, Plate 22, page 22 (Wilson) and Cardinal Red, Plate 822/3, page 168 (Wilson).

*Sepals.*—Inner surface—with fine, woolly tomentum. Outer surface—usually smooth; occasionally with a few stipitate glands. Alternate margins—lined with stipitate glands, and with none to few slender foliaceous appendages. Other margins—lined with fine, woolly tomentum.

*As first petal opens.*—Size—small. Form—medium length; broadly obovate. Color: outside—near Crimson, Plate 22/1, page 22 (Wilson), with small area at base of petal near Aureolin, Plate 3/2, page 3 (Wilson), and occasionally petal has lighter colored streak from base toward apex; inside—near Rose Madder, Plate 23, page 23 (Wilson), with small area at base of petal near Aureolin, Plate 3/2, page 3 (Wilson), and occasional petal has lighter colored streak from base toward apex.

*Opening.*—Opens up well; is not retarded from opening by cold, hot, wet or dry weather.

Bloom:

*Size (when fully open).*—Small; from 2½ inches to 3½ inches.

*Petalage.*—Semi-double; from 8 to 10 petals, plus 1 or 2 petaloids; arranged regularly.

*Form.*—High-centered at first, but becoming flat; petals being at first loosely cupped, but becoming later at maturity more loosely flat.

Petals:

*Texture.*—Moderately leathery. Inside—from satiny to velvety. Outside—satiny.

*Shape.*—Outer—broadly obovate, with apex flat. Inner—broadly obovate, with irregular margins, and with apex from rounded to flat.

This description of a newly opened flower was made from a rose grown outdoors in the month of October at Ontario, California:

*Color.*—Outer petal: outside surface—between Rose Madder, Plate 23/1, page 23 (Wilson) and Tyrian Rose, Plate 24/1, page 24 (Wilson), with small area at base near Canary Yellow, Plate 2/3, page 2 (Wilson); inside surface—between Tyrian Rose, Plate 24/1, page 24 (Wilson) and Phlox Pink, Plate 625, page 77 (Wilson), with small area at base near Canary Yellow, Plate 2/2, page 2 (Wilson). Inner petal: outside surface—near Rose Madder, Plate 23/1, page 23 (Wilson), with small area at base near Canary Yellow, Plate 2/3, page 2 (Wilson); inside surface—between Rose Madder, Plate 23, page 23 (Wilson) and Rose Madder, Plate 23/1, page 23 (Wilson), with small area at base near Canary Yellow, Plate 2/2, page 2 (Wilson).

This description was made from a rose that was open for 3 days outdoors in the month of October at Ontario, California:

*Color*: Outer petal: outside surface—near Phlox Pink, Plate 625/1, page 77 (Wilson), fading to near Phlox Pink, Plate 625/3, page 77 (Wilson) toward base, with small area at base near Empire Yellow, Plate 603/3, page 66 (Wilson); inside surface—near Phlox Pink, Plate 625, page 77 (Wilson), fading to near Phlox Pink, Plate 625/3, page 77 (Wilson) toward base, with small area at base near Empire Yellow, Plate 603/3, page 66 (Wilson). Inner petal: outside surface—near Phlox Pink, Plate 625/1, page 77 (Wilson), fading to near Phlox Pink, Plate 625/3, page 77 (Wilson) toward base, with small area at base near Empire Yellow, Plate 603/3, page 66 (Wilson); inside surface—near Phlox Pink, Plate 625, page 77 (Wilson), fading to near Phlox Pink, Plate 625/3, page 77 (Wilson) toward base, with small area at base near Empire Yellow, Plate 603/3, page 66 (Wilson).

*General color effect.*—Newly opened flower—between Rose Madder, Plate 23, page 23 (Wilson) and Tyrian Rose, Plate 24/1, page 24 (Wilson). 3-days open—between Phlox Pink, Plate 625, page 77 (Wilson) and Phlox Pink, Plate 625/1, page 77 (Wilson); later usually fading to still a lighter color between white and Rhodamine Pink, Plate 527/3, page 138 (Wilson).

*Behavior.*—Drop off cleanly; not particularly affected by cold, hot, wet or dry weather.

*Flower longevity.*—On bush in garden—from 3 to 5 days in October. Cut roses grown outdoors and kept at living-room temperatures—2 or 3 days in October.

*Reproductive organs*

Stamens: Average number; arranged regularly about pistils.

Filaments: From short to medium length; from 3 to 12 mm. in length; most with anthers. Color—near Lemon Yellow, Plate 4/1, page 4 (Wilson).

Anthers: Small; all open approximately at once. Color: upper side—margins near Yellow Ochre, Plate 07, page 101 (Wilson), with remainder near Lemon Yellow, Plate 4/1, page 4 (Wilson); under side—margins near Yellow Ochre, Plate 07/1, page 101 (Wilson), with remainder near Lemon Yellow, Plate 4/1, page 4 (Wilson).

Pollen: Abundant. Color—near Cadmium Orange, Plate 8/1, page 8 (Wilson).

Pistils: Few; approximately 25 in number.

Styles: Moderately even; from short to average length; from 6 to 8 mm. in length; from thin to average caliper; columnar; hairy. Color—near Dresden Yellow, Plate 64/3, page 64 (Wilson), with upper ⅓ of styles overlaid with near Carmine, Plate 21/3, page 21 (Wilson).

Stigma: Color—near Primrose Yellow, Plate 601/1, page 65 (Wilson).

Ovaries: Usually all enclosed in calyx.

Hips: Short; globular; smooth; walls thick and fleshy. Color (mature)—near Apricot Orange, Plate XIV (Ridgway).

Sepals: Falling soon; from short to medium length; reflexed. Color: inside—near Light Grape Green, Plate XLI (Ridgway); outside—near Absinthe Green, Plate XXXI (Ridgway).

Seeds: Average number; from 6 to 10 per hip; usually medium size.

*Plant*

Foliage:

*Leaves.*—Compound of usually 3 to 7 leaflets; from normal quantity to abundant; medium size; leathery; semi-glossy.

*Leaflets.*—Shape—from oval to oblong, with apex acute. Base—round. Margin—simply Serrate.

*Color.*—Mature: upper surface—between Dark Dull Yellow Green, Plate XXXII (Ridgway) and Empire Green, Plate XXXII (Ridgway); under surface—near Asphodel Green, Plate XLI (Ridgway). Young: upper surface—between Olive Brown, Plate XL (Ridgway) and Deep Olive, Plate XL (Ridgway); under surface—between Deep Corinthian Red, Plate XXVII (Ridgway) and Ocher Red, Plate XXVII (Ridgway).

*Rachis (the supporting stem of the compound leaf).*—Average size. Upper side—grooved; with some stipitate glands on edges. Under side—smooth; with few stipitate glands and from 2 to 4 small prickles.

*Stipules.*—Medium length; medium width; with points of from short to medium length turning out at an angle of less than 45°.

*Disease resistance.*—Better-than-average resistance to mildew as compared with other varieties grown under comparable cultural conditions at Ontario, California.

Growth:

*Habit.*—Bushy; upright-spreading; much-branched.

*Growth.*—From very free to vigorous.

*Canes.*—Medium caliper.

*Main stems.*—Color—between Parrot Green, Plate VI (Ridgway) and Cedar Green, Plate VI (Ridgway). Large prickles—several; short; hooked slightly downward; with long, narrow base; color—near Mikado Brown, Plate XXIX (Ridgway). Small prickles—very few; color—near Mikado Brown, Plate XXIX (Ridgway). Hairs—none.

*Branches.*—Color—near Biscay Green, Plate XVII (Ridgway). Large prickles—several; shorts; hooked slightly downward; with narrow base of medium length; color—near Sayal Brown, Plate XXIX (Ridgway). Small prickles—very few; color—near Sayal Brown, Plate XXIX (Ridgway). Hairs—none.

*New shoots.*—Color—near Mignonette Green, Plate XXXI (Ridgway), overlaid with near Buffy Olive, Plate XXX (Ridgway) on side exposed to the sun. Large prickles—several; medium length; hooked slightly downward; with narrow base of medium length; color—near Ocher Red, Plate XXVII (Ridgway). Small prickles—few; color—near Ocher Red, Plate XXVII (Ridgway). Hairs—none.

I claim:

A new and distinct variety of rose plant of the floribunda class, substantially as herein shown and described, characterized particularly as to novelty by the unique combination of a vigorous, bushy, much-branched, and well-shaped plant habit, attractive, medium-sized, disease-resistant dark green foliage, a better-than average floriferousness with consequent complete coverage of the plant with flowers at peak bloom, and attractive, medium-sized, relatively flat flowers varying from medium to dark pink in general color tonality when first open but fading to a very light pink color as the petals drop, and presenting an attractive contrast of light and dark pink colors.

No references cited.